United States Patent [19]

Oda et al.

[11] Patent Number: 4,728,078
[45] Date of Patent: Mar. 1, 1988

[54] CERAMIC VALVE SEATS

[75] Inventors: Isao Oda; Yoshihiko Ishida, both of Nagoya, Japan

[73] Assignee: NGK Insulators, Ltd., Japan

[21] Appl. No.: 80,068

[22] Filed: Jul. 31, 1987

[30] Foreign Application Priority Data

Aug. 8, 1986 [JP] Japan ............................ 61-185336

[51] Int. Cl.$^4$ ............................................. F16K 31/00
[52] U.S. Cl. .................................... 351/360; 251/368; 123/188 S
[58] Field of Search ............................. 251/360, 368; 123/188 AA, 188 S

[56] References Cited

U.S. PATENT DOCUMENTS

| | | |
|---|---|---|
| 1,949,613 | 3/1934 | McDonald . |
| 2,447,858 | 8/1948 | Hoern ............................ 123/188 S |
| 2,665,675 | 1/1954 | Sheppard ........................ 123/188 S |
| 2,695,628 | 11/1954 | Wheildon ....................... 251/368 X |
| 2,753,858 | 7/1956 | Honeyman et al. . |
| 2,753,859 | 7/1956 | Bartlett . |
| 3,487,823 | 1/1970 | Tarter et al. . |
| 3,658,295 | 4/1972 | Paine ............................... 251/360 |
| 3,871,616 | 3/1975 | Taylor ........................ 251/368 X |
| 4,546,737 | 10/1985 | Kazuoka et al. . |
| 4,554,897 | 11/1985 | Yamada ...................... 123/188 S X |
| 4,556,022 | 12/1985 | Yamada et al. . |

FOREIGN PATENT DOCUMENTS 3506069 9/1985 Fed. Rep. of Germany .
60-104707 6/1985 Japan .

Primary Examiner—Harold W. Weakley
Attorney, Agent, or Firm—Parkhurst & Oliff

[57] ABSTRACT

A ceramic valve seat is disclosed herein. A face portion of the valve seat at which the valve seat is to contact with a valve is made of a ceramic material. At least edge portions of the valve-contacting face portion of the valve seat are rounded. By so constructing, impact force due to contact between the valve and the valve seat and stress concentration can be mitigated.

12 Claims, 3 Drawing Figures

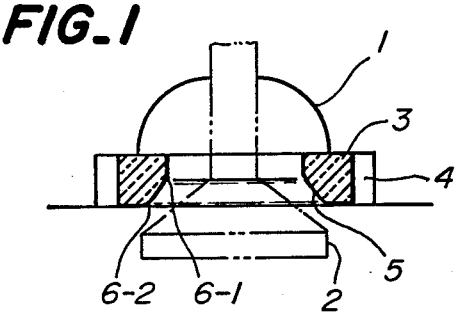
FIG._1
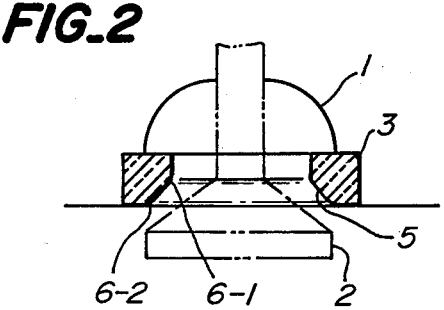
FIG._2
FIG._3
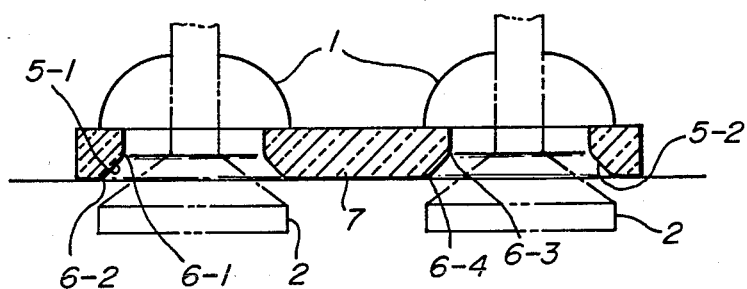

CERAMIC VALVE SEATS

BACKGROUND OF THE INVENTION (1) Field of the Invention

The present invention relates to ceramic value seats for use as valve-contacting faces in engine cylinder heads.

(2) Related Art Statement

Since the valve seats used in internal combustion engines are exposed to high temperatures and worn due to repeated loading of the valves, it has been attempted to use heat resisting alloys or ceramics for valve seat materials.

However, it has become difficult for valve seats made of heat resisting alloys to satisfy operating conditions at high temperatures and high pressures which have been severer year by year and to bear wearing conditions due to repeated loading, and mean time between overhaulings unfavorably decreases.

Although the valve seats made of ceramic materials can solve the above-mentioned shortcomings of the valve seats made of the heat resisting alloys, a stress concentration, at edge portions of the valve-contacting face of the valve seat, is likely to occur. Consequently, the ceramic valve seats have the drawbacks that the valve seats crack or fracture in an extreme case.

SUMMARY OF THE INVENTION

It is an object of the present invention to solve the above-mentioned problems, and to provide ceramic valve seats which have a smaller breakage risk and can withstand high temperatures and repeated loading.

The ceramic valve seat according to the present invention is characterized in that at least a valve-contacting face of the valve seat is made of a ceramic material and edge portions of the valve-contacting face of the valve seat are rounded.

If the edge portion of the valve-contacting face of the valve seat is not rounded and when the valve is seated on the valve-contacting face of the ceramic valve seat, a compressing surface pressure acts upon a portion of the ceramic valve seat being in contact with the valve while no surface pressure acts upon a non-contact portion thereof. That is, since the pressure discontinuously varies at a boundary between the valve-contacting portion and the valve non-contacting portion, a great shearing force acts upon the boundary. By rounding the edge portions of the valve-contacting face of the ceramic valve seat as in the present invention, variations in the surface pressure at the boundary between the valve-contacting face and the valve non-contacting portion are reduced when the valve is seated. Thus, the shearing force generated at the boundary can be lowered to effectively restrain occurrence of cracks.

In order to mitigate the stress concentration, it is effective to enlarge a radius of curvature of a section of the rounded edge portion. It is effective that the radius of curvature is not less than 0.1 mm at the minimum. When it is set at not less than 0.2 mm at minimum, the maximum stress-mitigating effect can be obtained. Therefore, it is preferable that the radius of curvature of the section profile of the rounded edge portion is set not less than 0.2 mm.

These and other objects, features and advantages of the present invention will be appreciated upon reading of the following description of the invention when taken in conjunction with the attached drawing, without understanding that some modifications, variations and changes of the same could be made by the skilled person in the art to which the invention pertains without departing from the spirit of the invention or the scope of claims appended hereto.

BRIEF DESCRIPTION OF THE DRAWING

For a better understanding of the invention, reference is made to the attached drawings, wherein:

FIG. 1 is a partial sectional view of an embodiment in which a ceramic valve seat according to the present invention is assembled into a cylinder head; and FIGS. 2 and 3 are partial sectional views of other embodiments in which a ceramic valve seat according to the present invention is assembled into a cylinder head.

DETAILED DESCRIPTION OF THE INVENTION

In order to produce a ceramic valve seat according to the present invention, a ceramic ring manufactured with a desired surface roughness in a desired shape is first prepared according to a conventional method. Next, an inner peripheral surface of the ceramic ring is formed with a valve-contacting face to be in conformity with a shape of a valve to be used. The ceramic valve seat is finally obtained by rounding edge portions of the valve-contacting face.

As a rounded sectional shape of the edge portion, an arc, an elliptical shape, or other arbitrary smooth curves may be used.

The larger the surface roughness of the valve-contacting face of the valve seat, the higher the coefficient of friction between the valve and the valve seat, where a great contact stress is produced when the valve impinges on the valve seat. In order to reduce the friction, it is preferable that the surface roughness of the ceramic valve seat according to the present invention is smaller. A value of 1.6 $\mu$m Ra or less is more preferable, and particularly, 0.2 $\mu$m Ra or less is more preferable.

The ceramic valve seats according to the present invention include a ceramic valve seat in which a metallic ring is provided around the outer periphery of a ceramic ring, and also include a ceramic valve seat which is a part of a ceramic cover plate in a cylinder head and is worked to integrally form a valve-contacting face. In addition, selection of the ceramic material from the group consisting of silicon nitride, silicon carbide, sialon, zirconia, and alumina is preferable from the standpoint of heat resistance and wear resistance.

In the following, embodiments of the ceramic valve seat according to the present invention will be explained. They are merely illustrative of the invention, but should never be interpreted to limit the scope of the invention.

EXAMPLE 1

In FIG. 1, a ceramic valve seat is assembled into a cylinder head 1 together with a valve 2. The ceramic valve seat according to the present invention in which a metallic ring 4 was provided around the outer periphery of the ceramic ring 3 was prepared in the following way, and its performance was compared. First, a ceramic ring 3 having an inner diameter of 24.0 mm, an outer diameter of 29.5 mm and a height of 7.0 mm was prepared from silicon nitride according to a pressureless sintering method. All the surface of the ceramic ring 3 was finished to a roughness of 1.6 μm Ra. A metallic ring made of Incoloy was worked to a surface roughness of 1.6 μm Ra in a shape of an outer diameter of 33.0 mm, a thickness of 2.0 mm and a height of 7.0 mm. The metallic ring was press-fitted around the outer periphery of the ceramic ring at room temperature to form a cylinder of a two layer structure consisting of the silicon nitride inner member and the Incoloy outer member. In order to apply aging hardening to the Incoloy of the cylinder, the cylinder was heated at 720° C. for 8 hours in a vacuum furnace, and then a furnace temperature was lowered to 680° C. The cylinder was maintained at this temperature for 10 hours.

The cylinder was then finished at a height of 4.0 mm, and a contact face 5 against the valve 2 was inclined by an angle of 30°. Edge portions 6-1 and 6-2 at the valve-contacting face 5 were rounded at 0.2 mm R, thereby obtaining the ceramic valve seat according to the present invention. The surface roughness of the valve contacting face was finished to 0.2 μm Ra. The thus obtained valve seat was press fitted in a fitting hole of an engine head in the state that the outer diameter of the valve seat had been worked larger by 0.02 mm than the inner diameter of the fitting hole.

For comparison purpose, a ceramic valve seat of the same design was prepared except that edge portions 6-1 and 6-2 were not rounded. With respect to the thus obtained ceramic valve seats, compression tests were conducted. As a result, while cracks occurred at the non-rounded edge portions of the valve-contacting face of the comparison ceramic valve seat upon application of a 600 kg load, the ceramic valve seats according to the present invention was not broken even under application of 10 ton load. Thus, the latter exhibited more excellent compression characteristics as compared with the ceramic valve seat with the non-rounded edge portions. In the compression tests, a press jig was utilized. The jig was designed such that it might bring the valve into contact with only a small area of the edge portions of the valve seat in a simulation test for examining contact between the valve and the valve seat to concentrate stress on the edge portion. The above-mentioned compression tests were conducted while varying the radius of curvature of the edge portions, and results shown in Table 1 were obtained. The larger the radius of curvature, the larger the load causing the fracture. When the minimum radius of curvature is not less than 0.1 mm, a compression load 10 times as large as the above fracture load for non-rounded valve seat is needed for breakage. If the minimum radius of curvature is not less than 0.2 mm, no cracks occurred even under application of the compression load of 10 tons.

TABLE 1

| Minimum radius of curvature (mm) | Compression load (ton) | Results |
| --- | --- | --- |
| Edges being not rounded | 0.6 | cracked |
| 0.1 | 7 | cracked |
| 0.2 | 10 | no crack |
| 0.4 | 10 | no crack |
| 0.6 | 10 | no crack |

EXAMPLE 2

FIG. 2 shows a ceramic valve seat according to the present invention consisting of a ceramic ring 3 only which is assembled into a cylinder head 1 together with a valve 2. The ceramic valve seat was produced in the following way, and its performance was compared. That is, the ceramic valve seat according to the present invention consisting of only a zirconia ring 3 having the same shape and edge portions 6-1 and 6-2 rounded at the same minimum radius of curvature as in Example 1 was prepared, and a ceramic valve seat consisting of only a ring 3 made of zirconia and having edge portions not rounded was produced as comparison example. Each of the ceramic valve seats was designed to have an outer diameter larger by 0.02 mm than an inner diameter of a fitting hole, and was directly press fitted into the fitting hole of the engine cylinder head. The ceramic valve seat-fitted cylinder head was assembled into a diesel engine on test bed, which was subjected to a durability test with an engine speed of 2,300 rpm and BMEP 15.0 kg/cm². As a result, it was observed that the ceramic valve seat having the edge portions not rounded was cracked in 50 hours, but no cracks were observed after the 50 hours durability test in the case of the ceramic valve seat having the minimum radius of curvature of 0.2 mm according to the present invention.

EXAMPLE 3

A ceramic valve seat according to the present invention shown in FIG. 3 was prepared by integrally forming a ceramic cover plate 7 made of silicon nitride and having not smaller than a diameter of a cylinder and a valve seat on the side of a combustion chamber of a cylinder head 1, and its performance was examined. The ceramic cover plate 7 was fitted into the cylinder head 1 by directly press fitting the ceramic cover plate 7 having the outer diameter larger by 0.25 mm than the inner diameter of the fitting hole on the side of the head 1 thereinto. The valve-contact faces 5-1 and 5-2 and the edge portions 6-1, 6-2, 6-3 and 6-4 were finished as in the same way as in Example 1. A motoring durable test was carried out with an engine speed of b 2,300 rpm for durability test in the state the ceramic cover plate 7 was assembled into the cylinder head. No cracks were observed after 50 hours durability test.

As obvious from the above-detailed description of the invention, according to the present invention, the stress concentration due to the impact force during when the valve impinges upon the valve seat or due to heat of exhaust gases can be mitigated. Therefore, the ceramic valve seat which can withstand high temperatures and repeated load and is free from the occurrence of cracks can be obtained by the invention.

What is claimed is:

1. A ceramic valve seat wherein at least a face at which the ceramic valve seat is to contact with a valve is made of a ceramic material and edge portions of the face of the valve seat at which the valve seat and the valve contact with each other are rounded.

2. A ceramic valve seat according to claim 1, wherein the edge portions of the face of the valve seat at which the valve seat is to contact with the valve are rounded in a curve at a minimum radius of curvature of not less than 0.2 mm.

3. A ceramic valve seat according to claim 1, wherein the ceramic valve seat is made of a ceramic material selected from the group consisting of silicon nitride, silicon carbide, sialon, zirconia, and alumina.

4. A ceramic valve seat according to claim 2, wherein the ceramic valve seat is made of a ceramic material selected from the group consisting of silicon nitride, silicon carbide, sialon, zirconia, and alumina.

5. A ceramic valve seat according to claim 1, wherein said face further comprises a surface roughness of not greater than 1.6 micron Ra.

6. A ceramic valve seat according to claim 1, wherein said face further comprises a surface roughness of not greater than 0.2 micron Ra.

7. A ceramic valve seat according to claim 2, wherein said face further comprises a surface roughness of not greater than 1.6 micron Ra.

8. A ceramic valve seat according to claim 2, wherein said face further comprises a surface roughness of not greater than 0.2 micron Ra.

9. A ceramic valve seat according to claim 3, wherein said face further comprises a surface roughness of not greater than 1.6 micron Ra.

10. A ceramic valve seat according to claim 3, wherein said face further comprises a surface roughness of not greater than 0.2 micron Ra.

11. A ceramic valve seat according to claim 4, wherein said face further comprises a surface roughness of not greater than 1.6 micron Ra.

12. A ceramic valve seat according to claim 4, wherein said face further comprises a surface roughness of not greater than 0.2 micron Ra.

* * * * *